US006171590B1

(12) United States Patent
Howard et al.

(10) Patent No.: US 6,171,590 B1
(45) Date of Patent: Jan. 9, 2001

(54) CHEMOKINE RECEPTOR PEPTIDE FOR INDUCING AN IMMUNE RESPONSE

(75) Inventors: Maureen Howard, Los Altos Hills; Shrikant Deshpande, Fremont, both of CA (US); Walter Ferlin, Antibes (FR); Subhashini Arimilli, Fremont, CA (US)

(73) Assignee: Corixa Corporation, WA (US)

( * ) Notice: Under 35 U.S.C. 154(b), the term of this patent shall be extended for 0 days.

(21) Appl. No.: 09/164,186

(22) Filed: Sep. 30, 1998

(51) Int. Cl.[7] .......................... A61K 38/16; A61K 38/17; A61K 39/00; A61K 38/12; C07K 14/705

(52) U.S. Cl. .................................. 424/185.1; 424/184.1; 530/351; 514/2; 514/9; 514/12; 514/13

(58) Field of Search .............................. 424/184.1, 185.1, 424/85.1; 530/351; 514/2, 9, 12, 13

(56) References Cited

FOREIGN PATENT DOCUMENTS

| WO9725340 | 7/1997 | (WO) . | |
| WO9811218 | 3/1998 | (WO) | C12N/15/12 |
| WO9950299 | 10/1999 | (WO) | C07K/14/15 |

OTHER PUBLICATIONS

Qin et al. Journal of Clinical Investigations, vol. 101, pp. 746–754, Feb. 1998.*
Disis et al. The Journal of Immunology, vol. 156 pp. 3151–3158, May 1996.*
Oppenheim et al., "Properties of the Novel Proinflammatory Supergene "Intercrine" Cytokine Family," *Ann. Rev. Immunol.* 9:617–648 (1991).
Premack and Schall., "Chemokine receptors: Gateways to inflammation and infection," *Nat. Med.* 2:1174–1178 (1996).
Baggolini et al., "Interleukin–8 and Related Chemotactic Cytokines—CXC and CC Chemokines," *Adv. Immunol.* 55:97–179 (1994).
Gerard et al., "The pro–inflammatory seven–transmembrane segment receptors of the leukocyte," *Curr. Opin. Immunol.* 6:140–145 (1994).
Sallusto et al., "Flexible Programs of Chemokine Receptor Expression on Human Polarized T Helper 1 and 2 Lymphocyes," *J. Exp. Med.* 187:875–883 (1998).
Ransohoff et al., "Astrocyte expression of mRNA encoding cytokines IP–10 and JE/MCP–1 in experimental autoimmune encephalomyelitis," *FASEB J.* 7:592–600 (1993).
Glabinski et al., "Synchronous Synthesis of a and B –Chemokines by Cells of Diverse Lineage in the Central Nervous System of Mice with Relapses of Chronic Experimental Autoimmune Encephalomyelitis," *Am. J. Pathol.* 150:617–630 (1995).
Godiska et al., "Chemokine expression in murine experimental allergic encephalomyelitis," *J. Neuroimmunol.* 58:167–176 (1995).

Eng et al., "Inflammation in EAE: Role of Chemokine/Cytokine Expression by Resident and Infiltrating Cells," *Neurchem. Res.* 21:511–525 (1996).
Taub et al., "Recombinant Human Interferon–inducible Protein 10 is a Chemoattractant for Human Monocytes and T Lymphocytes and Promotes T Cell Adhesion to Endothelial Cells," *J. Exp. Med.* 177:1809–1814 (1993).
Carr et al., "Monocyte chemoattractant protein 1 acts as a T–lymphocyte chemoattractant," *Proc. Natl. Acad. Sci. USA* 91:3652–3656 (1994).
Farber, "Mig and IP–10: CXC chemokines that target lymphocytes," J. Leukoc. Biol. 61:246–257 (1997).
Wojcik et al., "Chronic Intrathecal Infusion of Phosphorothioate or Phosphodiester Antisense Oligonucleotides against Cytokine Responsive Gene–2/IP–10 in Experimental Allergic Encephalomyelitis of Lewis Rat," *J. Pharm. Exp. Ther.* 278:404–410 (1996).
Loetscher et al., "Chemokine Receptor Specific for IP10 and Mig: Struicture, Function, and Expression in Activated T–Lymphocytes," *J. Exp. Med.* 184:963–969 (1996).
GenBank CAB02143 (Z79783) G Protein [gi:2281710] Jul. 26, 1997.
GenBank AAC40163 (AF045146) chemoki [gi:3282810] Jul. 9, 1998.
Bonecchi et al., "Differential Expression of Chemokine Receptors and Chemotactic Responsiveness of Type 1 T Helper Cells (Th1s) and Th2s," *J. Exp. Med.* 187:129–134 (1998).
Westmoreland, S. et al., "Chemokine Receptor Expression on Resident and Inflammatory Cells in the Brain of Macaques with Simian Immunodeficiency Virus Encephalitis," *Amer. J. Path.* 152:3, 659–665 (1998).
Disis, M. et al., "Peptide–Based, but Not Whole Protein, Vaccines Elicit Immunity to HER–2/neu, an Oncogenic Self–Profein," *Amer. Assoc. Immunol.*, 3151–3158 (1996).
Qin, S. et al. "The Chemokine Receptors CXCR3 and CCR5 Mark Subsets of T Cells Associated with Certain Inflammatory Reactions," *J. Clin. Invest.*, 101:4, 746–754 (1998).
Marchese et al., "Cloning and chromosomal mapping of three novel genes, GPR9, GPR10, and GPR14, encoding receptors related to interleukin 8, neuropeptide Y, and somatostatin receptors," Genomics 29:335 (1995).

* cited by examiner

*Primary Examiner*—Prema Mertz
*Assistant Examiner*—Fozia Hamud
(74) *Attorney, Agent, or Firm*—Townsend and Townsend Crew LLP (57) ABSTRACT

The present invention provides immunogenic oligopeptides derived from the chemokine receptor protein for use in compositions and methods for the treatment, and prevention of inflammatory responses.

42 Claims, 4 Drawing Sheets

SEQUENCE LISTING

```
<160> NUMBER OF SEQ ID NOS: 17

<210> SEQ ID NO 1
<211> LENGTH: 20
<212> TYPE: PRT
<213> ORGANISM: Artificial Sequence
<220> FEATURE:
<223> OTHER INFORMATION: Description of Artificial Sequence:SP-1-1
      surface portion peptide from the extracellular region of
      the G-protein coupled human CXCR3 chemokine
      receptor

<400> SEQUENCE: 1

Met Val Leu Glu Val Ser Asp His Gln Val Leu Asn Asp Ala Glu Val
  1               5                  10                  15

Ala Ala Leu Leu
             20

<210> SEQ ID NO 2
<211> LENGTH: 20
<212> TYPE: PRT
<213> ORGANISM: Artificial Sequence
<220> FEATURE:
<223> OTHER INFORMATION: Description of Artificial Sequence:SP-1-2
      surface portion peptide from the extracellular region of
      the G-protein coupled human CXCR3 chemokine
      receptor

<400> SEQUENCE: 2

Glu Asn Phe Ser Ser Ser Tyr Asp Tyr Gly Glu Asn Glu Ser Asp Ser
  1               5                  10                  15
```

```
Cys Cys Thr Ser
            20

<210> SEQ ID NO 3
<211> LENGTH: 18
<212> TYPE: PRT
<213> ORGANISM: Artificial Sequence
<220> FEATURE:
<223> OTHER INFORMATION: Description of Artificial Sequence:SP-1-3
      surface portion peptide from the extracellular region of
      the G-protein coupled human CXCR3 chemokine
      receptor

<400> SEQUENCE: 3

Pro Pro Cys Pro Gln Asp Phe Ser Leu Asn Phe Asp Arg Ala Phe Leu
 1               5                  10                  15

Pro Ala

<210> SEQ ID NO 4
<211> LENGTH: 15
<212> TYPE: PRT
<213> ORGANISM: Artificial Sequence
<220> FEATURE:
<223> OTHER INFORMATION: Description of Artificial Sequence:SP-2-1
      surface portion peptide from the extracellular region of
      the G-protein coupled human CXCR3 chemokine
      receptor

<400> SEQUENCE: 4

Asp Ala Ala Val Gln Trp Val Phe Gly Ser Gly Leu Cys Lys Val
 1               5                  10                  15

<210> SEQ ID NO 5
<211> LENGTH: 16
<212> TYPE: PRT
<213> ORGANISM: Artificial Sequence
<220> FEATURE:
<223> OTHER INFORMATION: Description of Artificial Sequence:SP-3-1
      surface portion peptide from the extracellular region of
      the G-protein coupled human CXCR3 chemokine
      receptor

<400> SEQUENCE: 5

Ser Ala His His Asp Glu Arg Leu Asn Ala Thr His Cys Gln Tyr Asn
 1               5                  10                  15

<210> SEQ ID NO 6
<211> LENGTH: 17
<212> TYPE: PRT
<213> ORGANISM: Artificial Sequence
<220> FEATURE:
<223> OTHER INFORMATION: Description of Artificial Sequence:SP-3-2
      surface portion peptide from the extracellular region of
      the G-protein coupled human CXCR3 chemokine
      receptor

<400> SEQUENCE: 6

Phe Pro Gln Val Gly Arg Thr Ala Leu Arg Val Leu Gln Leu Val Ala
 1               5                  10                  15

Gly

<210> SEQ ID NO 7
<211> LENGTH: 24
<212> TYPE: PRT
<213> ORGANISM: Artificial Sequence
<220> FEATURE:
<223> OTHER INFORMATION: Description of Artificial Sequence:SP-4-1
``` surface portion peptide from the extracellular region of
the G-protein coupled human CXCR3 chemokine
receptor

<400> SEQUENCE: 7

Asp Ile Leu Met Asp Leu Gly Ala Leu Ala Arg Asn Cys Gly Arg Glu
1               5                   10                  15

Ser Arg Val Asp Val Ala Lys Ser
            20

<210> SEQ ID NO 8
<211> LENGTH: 58
<212> TYPE: PRT
<213> ORGANISM: Artificial Sequence
<220> FEATURE:
<223> OTHER INFORMATION: Description of Artificial Sequence:
      extracellular domain of the G-protein coupled human CXCR3
      chemokine receptor

<400> SEQUENCE: 8

Met Val Leu Glu Val Ser Asp His Gln Val Leu Asn Asp Ala Glu Val
1               5                   10                  15

Ala Ala Leu Leu Glu Asn Phe Ser Ser Ser Tyr Asp Tyr Gly Glu Asn
            20                  25                  30

Glu Ser Asp Ser Cys Cys Thr Ser Pro Pro Cys Pro Gln Asp Phe Ser
        35                  40                  45

Leu Asn Phe Asp Arg Ala Phe Leu Pro Ala
        50                  55

<210> SEQ ID NO 9
<211> LENGTH: 33
<212> TYPE: PRT
<213> ORGANISM: Artificial Sequence
<220> FEATURE:
<223> OTHER INFORMATION: Description of Artificial Sequence:
      extracellular domain of the G-protein coupled human CXCR3
      chemokine receptor

<400> SEQUENCE: 9

Ser Ala His His Asp Glu Arg Leu Asn Ala Thr His Cys Gln Tyr Asn
1               5                   10                  15

Phe Pro Gln Val Gly Arg Thr Ala Leu Arg Val Leu Gln Leu Val Ala
            20                  25                  30

Gly

<210> SEQ ID NO 10
<211> LENGTH: 20
<212> TYPE: PRT
<213> ORGANISM: Artificial Sequence
<220> FEATURE:
<223> OTHER INFORMATION: Description of Artificial Sequence:SP-1-1
      peptide amidated at the C terminus
<220> FEATURE:
<221> NAME/KEY: MOD_RES
<222> LOCATION: (20)
<223> OTHER INFORMATION: Xaa = leucinamide

<400> SEQUENCE: 10

Met Val Leu Glu Val Ser Asp His Gln Val Leu Asn Asp Ala Glu Val
1               5                   10                  15

Ala Ala Leu Xaa
            20

<210> SEQ ID NO 11

```
<211> LENGTH: 20
<212> TYPE: PRT
<213> ORGANISM: Artificial Sequence
<220> FEATURE:
<223> OTHER INFORMATION: Description of Artificial Sequence:SP-1-2
      peptide amidated at the C terminus
<220> FEATURE:
<221> NAME/KEY: MOD_RES
<222> LOCATION: (20)
<223> OTHER INFORMATION: Xaa = serinamide

<400> SEQUENCE: 11

Glu Asn Phe Ser Ser Ser Tyr Asp Tyr Gly Glu Asn Glu Ser Asp Ser
 1               5                  10                  15

Cys Cys Thr Xaa
            20

<210> SEQ ID NO 12
<211> LENGTH: 18
<212> TYPE: PRT
<213> ORGANISM: Artificial Sequence
<220> FEATURE:
<223> OTHER INFORMATION: Description of Artificial Sequence:SP-1-3
      peptide amidated at the C terminus
<220> FEATURE:
<221> NAME/KEY: MOD_RES
<222> LOCATION: (18)
<223> OTHER INFORMATION: Xaa = alaninamide

<400> SEQUENCE: 12

Pro Pro Cys Pro Gln Asp Phe Ser Leu Asn Phe Asp Arg Ala Phe Leu
 1               5                  10                  15

Pro Xaa

<210> SEQ ID NO 13
<211> LENGTH: 15
<212> TYPE: PRT
<213> ORGANISM: Artificial Sequence
<220> FEATURE:
<223> OTHER INFORMATION: Description of Artificial Sequence:SP-2-1
      peptide amidated at the C terminus
<220> FEATURE:
<221> NAME/KEY: MOD_RES
<222> LOCATION: (15)
<223> OTHER INFORMATION: Xaa = valinamide

<400> SEQUENCE: 13

Asp Ala Ala Val Gln Trp Val Phe Gly Ser Gly Leu Cys Lys Xaa
 1               5                  10                  15

<210> SEQ ID NO 14
<211> LENGTH: 16
<212> TYPE: PRT
<213> ORGANISM: Artificial Sequence
<220> FEATURE:
<223> OTHER INFORMATION: Description of Artificial Sequence:SP-3-1
      peptide amidated at the C terminus
<220> FEATURE:
<221> NAME/KEY: MOD_RES
<222> LOCATION: (16)
<223> OTHER INFORMATION: Xaa = asparaginamide

<400> SEQUENCE: 14

Ser Ala His His Asp Glu Arg Leu Asn Ala Thr His Cys Gln Tyr Xaa
 1               5                  10                  15

<210> SEQ ID NO 15
<211> LENGTH: 17
<212> TYPE: PRT
```

-continued

```
<213> ORGANISM: Artificial Sequence
<220> FEATURE:
<223> OTHER INFORMATION: Description of Artificial Sequence:SP-3-2
      peptide amidated at the C terminus
<220> FEATURE:
<221> NAME/KEY: MOD_RES
<222> LOCATION: (17)
<223> OTHER INFORMATION: Xaa = glycinamide

<400> SEQUENCE: 15

Phe Pro Gln Val Gly Arg Thr Ala Leu Arg Val Leu Gln Leu Val Ala
 1               5                  10                  15

Xaa

<210> SEQ ID NO 16
<211> LENGTH: 24
<212> TYPE: PRT
<213> ORGANISM: Artificial Sequence
<220> FEATURE:
<223> OTHER INFORMATION: Description of Artificial Sequence:SP-4-1
      peptide amidated at the C terminus
<220> FEATURE:
<221> NAME/KEY: MOD_RES
<222> LOCATION: (24)
<223> OTHER INFORMATION: Xaa = serinamide

<400> SEQUENCE: 16

Asp Ile Leu Met Asp Leu Gly Ala Leu Ala Arg Asn Cys Gly Arg Glu
 1               5                  10                  15

Ser Arg Val Asp Val Ala Lys Xaa
                20

<210> SEQ ID NO 17
<211> LENGTH: 12
<212> TYPE: PRT
<213> ORGANISM: Artificial Sequence
<220> FEATURE:
<223> OTHER INFORMATION: Description of Artificial Sequence:proteolipid
      protein (PLP) 139-151 peptide amidated at the C
      terminus
<220> FEATURE:
<221> NAME/KEY: MOD_RES
<222> LOCATION: (12)
<223> OTHER INFORMATION: Xaa = phenylalaninamide

<400> SEQUENCE: 17

His Ser Leu Gly Trp Leu Gly His Pro Asp Lys Xaa
 1               5                  10
```

CHEMOKINE RECEPTOR PEPTIDE FOR INDUCING AN IMMUNE RESPONSE

BACKGROUND OF THE INVENTION

The present invention relates to novel compositions and methods for inhibiting inflammatory responses associated with autoimmune diseases. In particular, it relates to vaccination with peptides from the extracellular regions of chemokine receptor molecules.

Chemokines constitute a family of small molecular weight cytokines that are produced in inflammation and regulate leukocyte recruitment. These molecules are ligands for seven transmembrane G protein linked receptors that induce a signaling cascade costimulation for T cell activation in addition to participating in transendothelial migration of leukocytes (Oppenheim et al. *Ann. Rev. Immunol.* 9:617–648 (1991), Premback et al. *Nat. Med.* 2:1174–1178 (1996)). Two subfamilies of chemokines, referred to as CC and CXC, have been discovered. CC and CXC chemokines are distinct from each other in their N terminal amino acid sequence which starts either with cysteine-cysteine or cysteine-X-cysteine where X is typically another L-amino acid. They are also distinct in their binding pattern to their receptors. For example, the CC chemokines bind to CC receptors and not to CXC receptors and vice versa.

Different chemokines regulate the trafficking of distinct populations of hemopoietic cells by activating specific 7-transmembrane receptors expressed by these cells (Baggiolini et al. *Adv. Immunol.* 55:97–179 (1994); Gerard et al. *Curr. Opin. Immunol.* 6:140–145 (1994)). Recent publications indicate that the Th1 and Th2 subsets of regulatory T cells are uniquely characterized by the chemokine receptors CXCR3 and CCR3, respectively (Sallusto, et al. *J. Exp. Med.* 187:875–883 (1998); Bonecchi, et al. *J. Exp. Med.* 187:129–134 (1998); Qin, et al. *J. Clin Invest.* 101:746–754 (1998)). Several studies have correlated the expression of three specific chemokines, IP-10, RANTES, and MCP-1, produced by astrocytes in the CNS with the presence of inflammatory infiltration within this tissue during the early phase of EAE (Ransohoff, et al. *FASEB J.* 7:592–600 (1993); Glabinski et al. *Am. J. Pathol.* 150:617–630 (1995) Godiska, et al. *J. Neuroimmunol.* 58:167–176 (1995); and Eng et al. *Neurchem. Res.* 21:511–525 (1996)). While all three chemokines have been shown to be capable of recruiting T lymphocytes in certain experimental models, IP-10 has been demonstrated to be specific for this lineage of hemopoietic cells (Taub et al. *J. Exp. Med.* 177:1809–1814 (1993)); Carr, etal. *Proc. Natl. Acad. Sci. USA* 91:3652–3656 (1994); and Farber, *J. Leukoc. Biol.* 61:246–257 (1997). MBP-immunized rats intrathecaly infused with an antisense phosphorothioate oligonucleotide to crg-2 (the murine homologue of human IP-10) show reduced disease clinical score of EAE (Wojcik, et al. *J. Pharmacol. Exp. Ther.* 278:404–410 (1996)).

In addition, higher expression of some of the chemokine receptors such as CXCR3 on IL2 activated human T lymphocytes and not on resting T lymphocytes has been demonstrated (Loetscher et al. *J. Exp. Med.* 184:963–969 (1996)).

Multiple sclerosis (MS) is a T cell-dependent autoimmune disease caused by localized demyelination in the central nervous system (CNS), with only limited therapeutic options available to patients. Extensive investigation has indicated that these autoreactive T lymphocytes frequently, though not always, express the Th1 phenotype of high level production of IFNg, IL-2 and TNFa, with little to no IL-4, IL-5 and IL-10.

Current therapeutics for autoimmune diseases, such as MS, involve the use of antiinflammatory agents or general immunosuppressants. Prior art methods for controlling autoimmune disease fail to provide a simple self-mediated method for specifically eliminating inflammatory responses mediated by chemokines associated with the autoimmune responses. The present invention addresses these and other needs.

SUMMARY OF THE INVENTION

The present invention provides methods of inducing an immune response against a chemokine receptor molecule in a patient. The methods comprise administering to the patient an immunologically effective amount of a pharmaceutical composition comprising an adjuvant and an immunogenic chemokine receptor polypeptide from a extracellular region of a chemokine receptor molecule, for example CXCR3.

The immunogenic peptides are preferably conformationally constrained, for example by cyclization. The length of the immunogenic peptide is not critical to the invention. Typically, the peptide consists of between about 10 and about 50 residues, more often between about 15 and about 30 residues. Exemplary immunogenic peptides of the invention include MVLEVSDHQVLNDAEVAALL (SEQ ID NO:1), ENFSSSYDYGENESDSCCTS (SEQ ID NO:2), PPCPQDFSLNFDRAFLPA (SEQ ID NO:3), DAAVQWVFGSGLCKV (SEQ ID NO:4), SAHHDERLNATHCQYN (SEQ ID NO:5), FPQVGRTALRVLQLVAG (SEQ ID NO:6), and DILMDLGALARNCGRESRVDVAKS (SEQ ID NO:7).

The immunogenic peptides can be administered by any of a number of means. Typically they are administered parenterally. The adjuvant can be, for example, alum.

In preferred embodiments, the method are used to inhibit recruitment of T cells to inflammation sites in a patient. Typically the inflammatory response is associated with an autoimmune disease, such as multiple sclerosis.

The invention also provides pharmaceutical compositions suitable for use in the above methods.

Definitions

The term "peptide" is used interchangeably with "oligopeptide" or "polypeptide" in the present specification to designate a series of residues, typically L-amino acids, connected one to the other typically by peptide bonds between the α-amino and carbonyl groups of adjacent amino acids.

The term "cyclic peptide" refers to peptides in which the N-terminal residue is linked to the C-terminal residue either directly or through an intermediate. Examples of links between the two residues include disulfide bonds and thioether linkages as described below.

An "immunogenic chemokine receptor polypeptide" of the present invention is a polypeptide capable of eliciting an immune response against a chemokine receptor molecule associated with inflammation in autoimmune responses in a patient, such as multiple sclerosis. As set forth in more detail below, the sequence of residues in the polypeptide will be identical to or substantially identical to a polypeptide sequence in a chemokine receptor molecule. Thus, a polypeptide of the invention that has a sequence "from a extracellular region of a chemokine receptor molecule" is polypeptide that has a sequence either identical to or substantially identical to the naturally occurring chemokine receptor amino acid sequence of the region.

Figure 1:
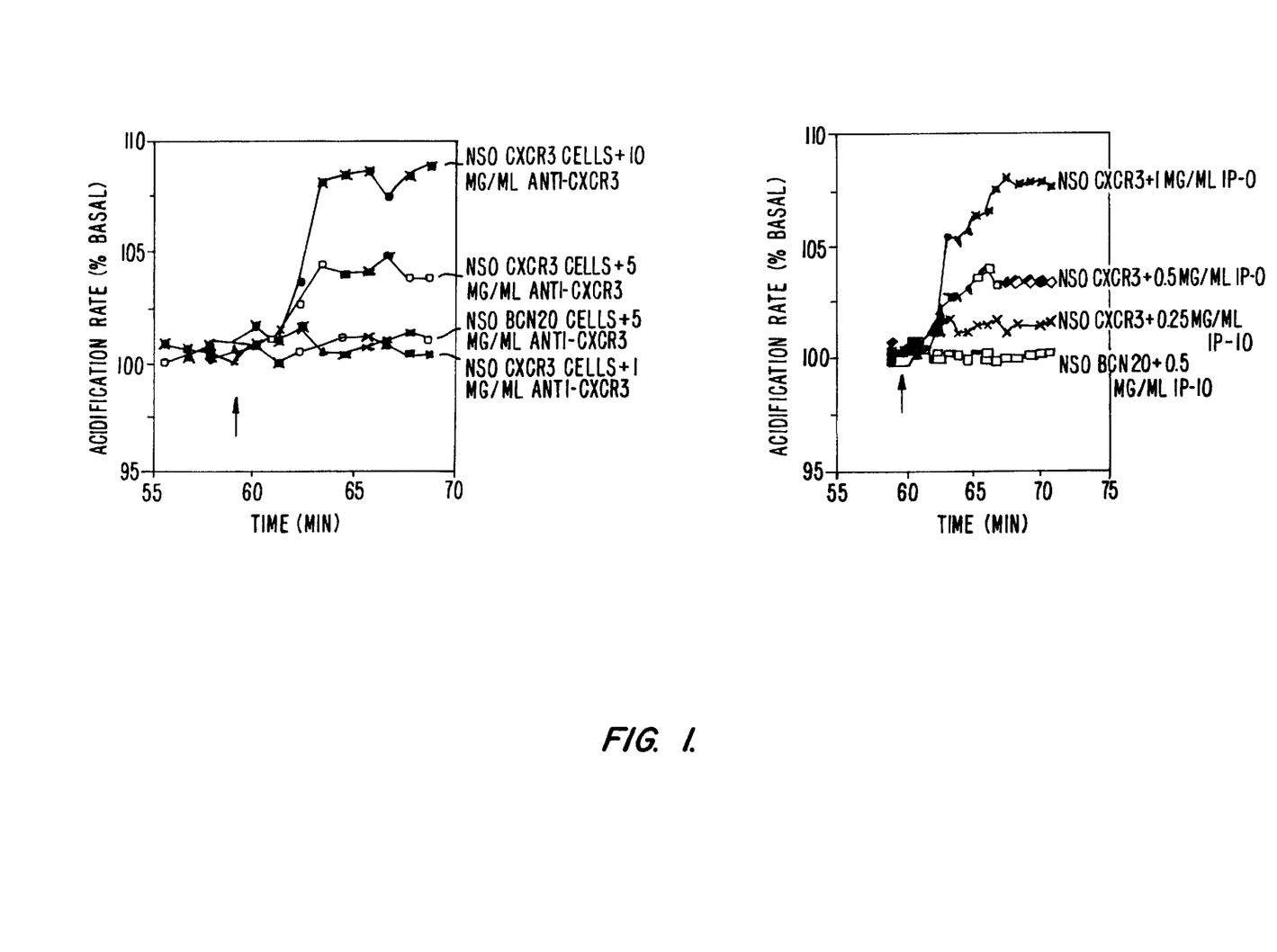
FIG. 1 shows acidification rate changes due to the binding of anti-human CXCR3 Mab or IP-10 to CXCR3-NSO transfectants. $5 \times 10^5$ CXCR3-NSO transfectant cells and untransfected "BONZO-NSO" cells (negative control) were spotted in the microphysiometer chambers along with agarose and 1, 5, 10 mglml anti-CXCR3 (FIG. 1a) or IP-10 (FIG. 1b) was pumped for 10 min. There is a dose dependent increase in the acidification rates with anti-CXCR3 in NSO-CXCR3 transfectant cells. Untransfected BONZO-NSO cells did not show any change in acidification rate changes either with the anti-CXCR3 antibody, or IP-10. The arrow indicates the time that ligands were added to the cells.

As used herein a "extracellular region" of a chemokine receptor molecule is a region of the molecule which is exposed on the surface of a cell expressing the native molecule. FIG. 1 provides a schematic of the extracellular domains of the human CXCR3 molecule. This molecule has four extracellular regions designated as SP-1, SP-2, SP-3 and SP-4, starting from the N-terminus.

As used herein, the term "adjuvant" refers to any substance which, when administered with or before an antigen, increases and/or qualitatively affects the immune response against the antigen in terms of antibody formation and/or the cell-mediated response. Exemplary adjuvants for use in the present invention are provided below.

The phrases "isolated" or "biologically pure" refer to material which is substantially or essentially free from components which normally accompany it as found in its native state. Thus, the chemokine receptor polypeptides of this invention do not contain materials normally associated with their in situ environment, e.g., other surface proteins on T cells. Even where a protein has been isolated to a homogenous or dominant band, there are trace contaminants in the range of 5–10% of native protein which co-purify with the desired protein. Isolated polypeptides of this invention do not contain such endogenous co-purified protein.

The term "residue" refers to an amino acid or amino acid mimetic incorporated in a oligopeptide by an amide bond or amide bond mimetic.

DESCRIPTION OF THE PREFERRED EMBODIMENTS

The present invention provides immunogenic polypeptides derived from chemokine receptor protein sequences for use in compositions and methods for the treatment and prevention of inflammatory responses. The polypeptides are capable of inducing an immune response against chemokine receptor molecules which mediate inflammatory responses associated with various diseases. In preferred embodiments the polypeptides of the invention are conformationally constrained (e.g., cyclized) and derived from extracellular regions of human CXCR3. Immunization with the polypeptides of the invention provides a specific immune response to particular chemokine receptors and results in the specific inhibition of the inflammatory responses mediated by these molecules.

The methods can be used to treat any inflammatory response mediated by chemokines. In particular, the methods are useful for treatment of autoimmune diseases, such as multiple sclerosis. Multiple sclerosis (MS), a human demyelinating disease which afflicts 600,000 individuals worldwide, results from damage of the myelin sheath of oligodendroglial cells in the Central Nervous System (CNS). Although the pathogenesis and etiology of MS have not yet been established, it is widely believed that the disease has an immunological basis and that both genetic and environmental factors make a contribution to the pathogenesis. The central mediator of autoimmune attack is believed to be host CD4+ T cells specific for one or more autoantigens in the CNS, with subsequent production of an array of tissue-destructive inflammatory mediators following autoantigen-activation of these cells. Indeed, immunohistochemical analysis of the focal plaques of demyelination which occur in the brains of MS patients as a consequence of MS pathology have revealed the presence of CD4+ T cells infiltrating these plaques.

Improved understanding of the immunopathological mechanisms underlying MS has developed from the study of experimental models of demyelination. The most commonly used model, experimental allergic encephalomyelitis (EAE), is an autoimmune inflammatory disorder of genetically susceptible mice that is mediated by autoantigen-specific CD4+ MHC class II restricted T cells. In susceptible SJL/J mice, the disease can display a relapsing-remitting clinical course of paralysis, which makes it an ideal system to study the efficacy of various immunoregulatory strategies both in the prevention and treatment of disease.

The current invention is focused not on the cytokine-producing phenotype of autoreactive T cells in this disease setting, but on their trafficking from the host circulation to the site of pathology, for example within the CNS in the case of MS. As noted above, hemopoietic cell migration is regulated by chemokines.

In some embodiments, the invention provides peptide vaccines against the 7-transmembrane chemokine receptor designated CXCR3. Consistent with the chemotactic fingerprint of IP-10, CXCR3 is expressed exclusively on activated effector T lymphocytes. Exemplary peptides of the invention include peptides derived from the extracellular domains of the CXCR3 protein are presented in Table 1.

In preferred embodiments, the peptides of the invention are cyclized. Methods for cyclizing peptides are described in detail below. In those cases in which the peptides are cyclized by disulfide linkages, one of skill will recognize that the peptides will further comprise cysteine residues either within the peptide or at each terminus.

Polypeptides suitable for use in the present invention can be obtained in a variety of ways. Conveniently, they can be synthesized by conventional techniques employing automatic synthesizers, such as the Beckman, Applied Biosystems, or other commonly available peptide synthesizers using well known protocols. They can also be synthesized manually using techniques well known in the art. See, e.g. Stewart and Young, *Solid Phase Peptide Synthesis*, (Rockford, Ill., Pierce), 2d Ed. (1984).

Alternatively, DNA sequences which encode the particular chemokine receptor polypeptide may be cloned and expressed to provide the peptide. Nucleic acid molecules encoding chemokine receptors are known in the art and sequences of such genes are available, for instance, from GenBank (see, e.g., GenBank Accession Nos. HSU83326 HSU97123, and AF005058).

Standard techniques can be used to screen cDNA libraries to identify sequences encoding the desired sequences (see, Sambrook et al., *Molecular Cloning—A Laboratory Manual*, Cold Spring Harbor Laboratory, Cold Spring Harbor, N.Y., 1989). Fusion proteins (those consisting of all or part of the amino acid sequences of two or more proteins) can be recombinantly produced. In addition, using in vitro mutagenesis techniques, unrelated proteins can be mutated to comprise the appropriate sequences.

Chemokine receptor proteins from a variety of natural sources are also conveniently isolated using standard protein purification techniques. Peptides can be purified by any of a variety of known techniques, including, for example, reverse phase high-performance liquid chromatography (BPLC), ion-exchange or immunoaffinity chromatography, separation by size, or electrophoresis (See, generally, Scopes, R., *Protein Purification*, Springer-Verlag, N.Y. (1982)).

It will be understood that the immunogenic chemokine receptor polypeptides of the present invention may be modified to provide a variety of desired attributes, e.g., improved pharmacological characteristics, while increasing or at least retaining substantially all of the biological activity of the unmodified peptide. For instance, the peptides can be modified by extending, decreasing the amino acid sequence of the peptide. Substitutions with different amino acids or amino acid mimetics can also be made.

The peptides employed in the subject invention need not be identical to peptides disclosed in the Example section, below, so long as the subject peptides are able to induce an immune response against the desired chemokine receptor molecule. Thus, one of skill will recognize that a number of conservative substitutions (described in more detail below) can be made without substantially affecting the activity of the peptide.

Single amino acid substitutions, deletions, or insertions can be used to determine which residues are relatively insensitive to modification. Substitutions are preferably made with small, relatively neutral moieties such as Ala, Gly, Pro, or similar residues. The effect of single amino acid substitutions may also be probed using D-amino acids. The number and types of residues which are substituted or added depend on the spacing necessary between essential contact points and certain functional attributes which are sought (e.g., hydrophobicity versus hydrophilicity). Increased immunogenicity may also be achieved by such substitutions, compared to the parent peptide. In any event, such substitutions should employ amino acid residues or other molecular fragments chosen to avoid, for example, steric and charge interference which might disrupt binding.

The substituting amino acids, however, need not be limited to those naturally occurring in proteins, such as L-α-amino acids, or their D-isomers. The peptides may be substituted with a variety of moieties such as amino acid mimetics well known to those of skill in the art.

The individual residues of the immunogenic chemokine receptor polypeptides can be incorporated in the peptide by a peptide bond or peptide bond mimetic. A peptide bond mimetic of the invention includes peptide backbone modifications well known to those skilled in the art. Such modifications include modifications of the amide nitrogen, the α-carbon, amide carbonyl, complete replacement of the amide bond, extensions, deletions or backbone crosslinks. See, generally, Spatola, *Chemistry and Biochemistry of Amino Acids, Peptides and Proteins*, Vol. VII (Weinstein ed., 1983). Several peptide backbone modifications are known, these include, $\psi[CH_2S]$, $\psi[CH_2NH]$, $\psi[CSNH_2]$, $\psi[NHCO]$, $\psi[COCH_2]$ and $\psi[(E)$ or $(Z)$ $CH=CH]$. The nomenclature used above, follows that suggested by Spatola, above. In this context, $\psi$ indicates the absence of an amide bond. The structure that replaces the amide group is specified within the brackets.

Amino acid mimetics may also be incorporated in the peptides. An "amino acid mimetic" as used here is a moiety other than a naturally occurring amino acid that conformationally and functionally serves as a substitute for an amino acid in a polypeptide of the present invention. Such a moiety serves as a substitute for an amino acid residue if it does not interfere with the ability of the peptide to illicit an immune response against the appropriate chemokine receptor molecule. Amino acid mimetics may include non-protein amino acids, such as β-γ-δ-amino acids, β-γ-δ-imino acids (such as piperidine-4-carboxylic acid) as well as many derivatives of L-α-amino acids. A number of suitable amino acid mimetics are known to the skilled artisan, they include cyclohexylalanine, 3-cyclohexylpropionic acid, L-adamantyl alanine, adamantylacetic acid and the like. Peptide mimetics suitable for peptides of the present invention are discussed by Morgan and Gainor, (1989) *Ann. Repts. Med. Chem.* 24:243–252.

As noted above, the peptides employed in the subject invention need not be identical, but may be substantially identical, to the corresponding sequence of the target chemokine receptor molecule. Therefore, the peptides may be subject to various changes, such as insertions, deletions, and substitutions, either conservative or non-conservative, where such changes might provide for certain advantages in their use. The polypeptides of the invention can be modified in a number of ways so long as they comprise a sequence substantially identical (as defined below) to a sequence in the target region of the chemokine receptor molecule.

Alignment and comparison of relatively short amino acid sequences (less than about 30 residues) is typically straightforward. Comparison of longer sequences may require more sophisticated methods to achieve optimal alignment of two sequences. Optimal alignment of sequences for aligning a comparison window may be conducted by the local homology algorithm of Smith and Waterman (1981) *Adv. Appl. Math.* 2:482, by the homology alignment algorithm of Needleman and Wunsch (1970) *J. Mol. Biol.* 48:443, by the search for similarity method of Pearson and Lipman (1988) *Proc. Natl. Acad. Sci. (USA)* 85:2444, by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of sequence similarity over the comparison window) generated by the various methods is selected.

The term "sequence identity" means that two polynucleotide sequences are identical (i.e., on a nucleotide-by-nucleotide basis) over a window of comparison. The term "percentage of sequence identity" is calculated by comparing two optimally aligned sequences over the window of comparison, determining the number of positions at which the identical residues occurs in both sequences to yield the number of matched positions, dividing the number of matched positions by the total number of positions in the window of comparison (i.e., the window size), and multiplying the result by 100 to yield the percentage of sequence identity.

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (e.g., 99 percent sequence identity). Preferably, residue positions which are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

The polypeptides of the invention typically comprise at least about 10 residues and more preferably at least about 15 residues from the extracellular domain of a chemokine receptor. In certain embodiments the peptides will not exceed about 50 residues and typically will not exceed about 30 residues. For instance, the peptides described below consist of about 15 to about 25 residues.

In the preferred embodiments of the invention, the immunogenic peptides are conformationally constrained. Means for achieving this are well known in the art (see, e.g., Hruby and Bonner in *Methods in Molecular Biology, Volume 35: Peptide Synthesis Protocols* Pennington and Dunn eds (Humana Press, Totowa N.J., 1994). A preferred means for preparing conformationally constrained peptides is through cyclization. Any method commonly used to produce cyclized oligopeptides can be used to produce the peptides of the invention. For example, in certain embodiments the peptides will include cysteine residues at both termini, which allow the production of cyclic peptides through disulfide linkages. Treatment of a such a peptide with an oxidizing agent such as oxygen, iodine or similar agent will produce a cyclic peptide which may be further purified using chromatographic or other methods of chemical purification. Construction of cyclic peptides can also be accomplished through thioether linkages. For instance, N-bromoacetyl-derivatized peptides can be reacted with sulfhydryl-containing residues, such as cysteine. Cyclization occurs by reaction of the free sulfhydryl of cysteine in the peptide with the bromoacetyl group to form a thioether linkage (Robey et al., *Anal. Biochem.* 177:373–7 (1989) and U.S. Pat. No. 5,066,716).

Other methods of constructing cyclic peptides are known to those skilled in the art. These include side chain-side chain, side chain-main chain and main chain-main chain cyclizations. In addition, linkers can be used to join the amino and carboxyl termini of a peptide. The linker is capable of forming covalent bonds to both the amino and carboxyl terminus. Suitable linkers are well known to those of skill in the art and include, but are not limited to, straight or branched-chain carbon linkers, heterocyclic carbon linkers, or peptide linkers. The linkers may be joined to the carboxyl and amino terminal amino acids through their side groups (e.g., through a disulfide linkage to cysteine) or through the alpha carbon amino and carboxyl groups of the terminal amino acids.

For a general discussion of suitable methods for cyclization see, Hruby and Bonner in *Methods in Molecular Biology, Volume 35: Peptide Synthesis Protocols* Pennington and Dunn eds (Humana Press, Totowa N.J., 1994). For instance, cyclizations may include formation of carba analogs and thioethers (Lebl et al. in *Peptides* 1986 Proceedings of the 19th European Peptide Symposium pp. 341–344; Robey et al., *Anal. Biochem.* 177:373–7 (1989) and U.S. Pat. No. 5,066,716), bis-thioethers (Mosberg et al. *JACS* 107:2986–2987 (1985)), azopeptides (Siemion et al. *Mol. Cell. Biochem.* 34: (1991)), and other cyclic structures, such as bridging structures (Charpentier, M., et al.,*J. Med. Chem.* 32(6):1184–1190 (1989), Thaisrivongs, S., et al., *J. Med. Chem.* 34(4):127 (1991) and Ozeki, E., et al.,*Int. J. Peptide Protein Res.* 34:111 (1989)). Cyclization from backbone-to-backbone positions may also be used.

Bridging is a special type of cyclization in which distant sites in a peptide are brought together using separate bridging molecules or fragments. Bridging molecules may include, for example, succinic anhydride molecules (Charpentier, B., et al., supra), and carboxymethylene fragments (Thaisrivongs, S., et al., supra). Bridging by metals can also be used (Ozeki, E., et al., supra).

In some embodiments, the peptides include two or more cystine residues. The cystines can be substituted or added within the peptide or at either terminus. The position of the cystines is not critical so long as disulfide linkages can form between them which allow the production of cyclic peptides. For example, treatment of such a peptide with an oxidizing agent such as oxygen, iodine or similar agent will produce a cyclic peptide which may be further purified using chromatographic or other methods of chemical purification.

In addition to use of peptides, antibodies raised against peptides of the invention can be used to inhibit inflammatory responses. Antibodies can be raised to the peptides of the present invention using techniques well known to those of skill in the art. Anti-idiotypic antibodies can also be generated. The following discussion is presented as a general overview of the techniques available; however, one of skill will recognize that many variations upon the following methods are known.

A number of immunogens can be used to produce antibodies specifically reactive with the peptides. For instance, the entire chemokine receptor molecule or fragments containing the desired sequence can be used. Synthetic peptides as disclosed here can be used either in linear form or cyclized.

Methods of producing polyclonal antibodies are known to those of skill in the art. In brief, an immunogen (antigen), preferably a purified polypeptide, a polypeptide coupled to an appropriate carrier (e.g., GST, keyhole limpet hemanocyanin, etc.), or a polypeptide incorporated into an immunization vector such as a recombinant vaccinia virus (see, U.S. Pat. No. 4,722,848) is mixed with an adjuvant and animals are immunized with the mixture. The animal's immune response to the immunogen preparation is monitored by taking test bleeds and determining the titer of reactivity to the polypeptide of interest. When appropriately high titers of antibody to the immunogen are obtained, blood is collected from the animal and antisera are prepared. Further fractionation of the antisera to enrich for antibodies reactive to the polypeptide is performed where desired (see, e.g., Coligan (1991) *Current Protocols in Immunology* Wiley/Greene, N.Y.; and Harlow and Lane (1989) *Antibodies: A Laboratory Manual* Cold Spring Harbor Press, N.Y.).

In some instances, it is desirable to prepare monoclonal antibodies from various mammalian hosts, such as mice, rodents, primates, humans, etc. Description of techniques for preparing such monoclonal antibodies are found in, e.g., Stites et al. (eds.) *Basic and Clinical Immunology* (4th ed.) Lange Medical Publications, Los Altos, Calif., and references cited therein; Harlow and Lane, Supra; Goding (1986) *Monoclonal Antibodies: Principles and Practice* (2d ed.) Academic Press, New York, N.Y.; and Kohler and Milstein (1975) *Nature* 256: 495–497. Summarized briefly, this method proceeds by injecting an animal with an immunogen. The animal is then sacrificed and cells taken from its spleen, which are fused with myeloma cells. The result is a hybrid cell or "hybridoma" that is capable of reproducing in vitro. The population of hybridomas is then screened to isolate individual clones, each of which secrete a single antibody species to the immunogen. In this manner, the individual antibody species obtained are the products of immortalized and cloned single B cells from the immune animal generated in response to a specific site recognized on the immunogenic substance.

Alternative methods of immortalization include transformation with Epstein Barr Virus, oncogenes, or retroviruses, or other methods known in the art. Colonies arising from single immortalized cells are screened for production of antibodies of the desired specificity and affinity for the antigen, and yield of the monoclonal antibodies produced by such cells is enhanced by various techniques, including injection into the peritoneal cavity of a vertebrate (preferably mammalian) host. Specific monoclonal and polyclonal antibodies will usually bind with a $K_D$ of at least about 0.1 mM, more usually at least about 50 $\mu$M, and most preferably at least about 1 $\mu$M or better.

Other suitable techniques involve selection of libraries of recombinant antibodies in phage or similar vectors (see, e.g., Huse et al. (1989) *Science* 246: 1275–1281; and Ward, et al. (1989) *Nature* 341: 544–546; and Vaughan et al. (1996) *Nature Biotechnology*, 14: 309–314).

Frequently, the peptides and antibodies of the invention will be labeled by joining, either covalently or noncovalently, a substance which provides for a detectable signal. A wide variety of labels and conjugation techniques are known and are reported extensively in both the scientific and patent literature. Suitable labels include radionucleotides, enzymes, substrates, cofactors, inhibitors, fluorescent moieties, chemiluminescent moieties, magnetic particles, and the like. Patents teaching the use of such labels include U.S. Pat. Nos. 3,817,837; 3,850,752; 3,939,350; 3,996,345; 4,277,437; 4,275,149; and 4,366,241. Also, recombinant immunoglobulins may be produced. See, Cabilly, U.S. Pat. No. 4,816,567; and Queen et al. (1989) *Proc. Nat'l Acad. Sci. USA* 86: 10029–10033.

The antibodies of this invention can also be administered to an organism (e.g., a human patient) for therapeutic purposes (e.g., to inhibit an autoimmune response). Antibodies administered to an organism other than the species in which they are raised are often immunogenic. Thus, for example, murine antibodies administered to a human often induce an immunologic response against the antibody (e.g., the human anti-mouse antibody (HAMA) response) on multiple administrations. The immunogenic properties of the antibody are reduced by altering portions, or all, of the antibody into characteristically human sequences thereby producing chimeric or human antibodies, respectively.

Chimeric antibodies are immunoglobulin molecules comprising a human and non-human portion. More specifically, the antigen combining region (or variable region) of a humanized chimeric antibody is derived from a non-human source (e.g., murine) and the constant region of the chimeric antibody (which confers biological effector function to the immunoglobulin) is derived from a human source. The chimeric antibody should have the antigen binding specificity of the non-human antibody molecule and the effector function conferred by the human antibody molecule. A large number of methods of generating chimeric antibodies are well known to those of skill in the art (see, e.g., U.S. Pat. Nos.: 5,502,167, 5,500,362, 5,491,088, 5,482,856, 5,472,693, 5,354,847, 5,292,867, 5,231,026, 5,204,244, 5,202,238, 5,169,939, 5,081,235, 5,075,431, and 4,975,369). An alternative approach is the generation of humanized antibodies by linking the CDR regions of non-human antibodies to human constant regions by recombinant DNA techniques. See Queen et al., *Proc. Natl. Acad. Sci. USA* 86:10029–10033 (1989) and WO 90/07861.

In one preferred embodiment, recombinant DNA vector is used to transfect a cell line that produces an antibody against a peptide of the invention. The novel recombinant DNA vector contains a "replacement gene" to replace all or a portion of the gene encoding the immunoglobulin constant region in the cell line (e.g., a replacement gene may encode all or a portion of a constant region of a human immunoglobulin, or a specific immunoglobuhin class), and a "target sequence" which allows for targeted homologous recombination with immunoglobulin sequences within the antibody producing cell.

In another embodiment, a recombinant DNA vector is used to transfect a cell line that produces an antibody having a desired effector function, (e.g., a constant region of a human immunoglobulin) in which case, the replacement gene contained in the recombinant vector may encode all or a portion of a region of an antibody and the target sequence contained in the recombinant vector allows for homologous recombination and targeted gene modification within the antibody producing cell. In either embodiment, when only a portion of the variable or constant region is replaced, the resulting chimeric antibody may define the same antigen and/or have the same effector function yet be altered or improved so that the chimeric antibody may demonstrate a greater antigen specificity, greater affinity binding constant, increased effector function, or increased secretion and production by the transfected antibody producing cell line, etc.

In another embodiment, this invention provides for fully human antibodies. Human antibodies consist entirely of characteristically human polypeptide sequences. The human antibodies of this invention can be produced in using a wide variety of methods (see, e.g., Larrick et al., U.S. Pat. No. 5,001,065). In one preferred embodiment, the human antibodies of the present invention are produced initially in trioma cells. Genes encoding the antibodies are then cloned and expressed in other cells, particularly, nonhuman mammalian cells. The general approach for producing human antibodies by trioma technology has been described by Ostberg et al. (1983), *Hybridoma* 2: 361–367, Ostberg, U.S. Pat. No. 4,634,664, and Engelman et al., U.S. Pat. No. 4,634,666. The antibody-producing cell lines obtained by this method are called triomas because they are descended from three cells; two human and one mouse. Triomas have been found to produce antibody more stably than ordinary hybridomas made from human cells.

Formulation and Administration

The peptides or antibodies (typically monoclonal antibodies) of the present invention and pharmaceutical compositions thereof are useful for administration to mammals, particularly humans, to treat and/or prevent deleterious immune inflammatory responses, particularly those associated with autoimmune responses. Over 30 autoimmune diseases are presently known, including myasthenia gravis (MG), multiple sclerosis (MS), systemic lupus erythematosis (SLE), rheumatoid arthritis (RA), insulin-dependent diabetes mellitus (IDDM), and the like. Suitable formulations are found in *Remington's Pharmaceutical Sciences*, Mack Publishing Company, Philadelphia, Pa., 17th ed. (1985).

The immunogenic peptides or antibodies of the invention are administered prophylactically or to an individual already suffering from the disease. The peptide compositions are administered to a patient in an amount sufficient to elicit an effective immune response to the chemokine receptor molecule from which the peptides are derived. An effective immune response is one that inhibits recruitment of T cells to sites of inflammation. An amount adequate to accomplish this is defined as "therapeutically effective dose" or "immunogenically effective dose." Amounts effective for this use will depend on, e.g., the peptide composition, the manner of administration, the stage and severity of the disease being treated, the weight and general state of health of the patient, and the judgment of the prescribing physician, but generally range for the initial immunization (that is for therapeutic or prophylactic administration) from about 0.1 mg to about 1.0 mg per 70 kilogram patient, more commonly from about 0.5 mg to about 0.75 mg per 70 kg of body weight. Boosting dosages are typically from about 0.1 mg to about 0.5 mg of peptide using a boosting regimen over weeks to months depending upon the patient's response and condition. A suitable protocol would include injection at time 0, 4, 2, 6, 10 and 14 weeks, followed by further booster injections at 24 and 28 weeks.

It must be kept in mind that the peptides and compositions of the present invention may generally be employed in serious disease states, that is, life-threatening or potentially life threatening situations. In such cases, in view of the minimization of extraneous substances and the relative nontoxic nature of the peptides, it is possible and may be felt desirable by the treating physician to administer substantial excesses of these peptide compositions.

For therapeutic use, administration should begin at the first sign of autoimmune disease. This is followed by boosting doses until at least symptoms are substantially abated and for a period thereafter. In some circumstances, loading doses followed by boosting doses may be required. The resulting immune response helps to cure or at least partially arrest symptoms and/or complications. Vaccine compositions containing the peptides are administered prophylactically to a patient susceptible to or otherwise at risk of the disease to elicit an immune response against the target Chemokine receptor antigen.

The pharmaceutical compositions (containing either peptides or antibodies) are intended for parenteral or oral administration. Preferably, the pharmaceutical compositions are administered parenterally, e.g., subcutaneously, intradermally, or intramuscularly. Thus, the invention provides compositions for parenteral administration which comprise a solution of the immunogenic peptides dissolved or suspended in an acceptable carrier, preferably an aqueous carrier. A variety of aqueous carriers may be used, e.g., water, buffered water, 0.4% saline, 0.3% glycine, hyaluronic acid and the like. These compositions may be sterilized by conventional, well known sterilization techniques, or may be sterile filtered. The resulting aqueous solutions may be packaged for use as is, or lyophilized, the lyophilized preparation being combined with a sterile solution prior to administration. The compositions may contain pharmaceutically acceptable auxiliary substances as required to approximate physiological conditions, such as buffering agents, tonicity adjusting agents, wetting agents and the like, for example, sodium acetate, sodium lactate, sodium chloride, potassium chloride, calcium chloride, sorbitan monolaurate, triethanolamine oleate, etc.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10–95% of active ingredient, that is, one or more peptides of the invention, and more preferably at a concentration of 25%–75%.

As noted above, the peptide compositions are intended to induce an immune response to the peptides. Thus, compositions and methods of administration suitable for maximizing the immune response are preferred. For instance, peptides may be introduced into a host, including humans, linked to a carrier or as a homopolymer or heteropolymer of active peptide units. Alternatively, the a "cocktail" of polypeptides can be used. A mixture of more than one polypeptide has the advantage of increased immunological reaction and, where different peptides are used to make up the polymer, the additional ability to induce antibodies to a number of epitopes. For instance, polypeptides comprising sequences from extracellular regions of α and β chains may be used in combination. Useful carriers are well known in the art, and include, e.g., KLH, thyroglobulin, albumins such as human serum albumin, tetanus toxoid, polyamino acids such as poly(lysine:glutamic acid), influenza, hepatitis B virus core protein, hepatitis B virus recombinant vaccine and the like.

The use of more than one polypeptide is particularly useful to enhance the immune response against polypeptides of the invention. As demonstrated below, although the polypeptides may be derived from self Chemokine receptor molecules expressed in the patient, they can induce an immune response. In some instances, the immune response to the self polypeptide may not be sufficiently strong. In these instances, it may be necessary to break tolerance to the polypeptide. The compositions may comprise one or more of the foreign polypeptides that are sufficiently similar to the self polypeptides to induce an immune response against both the foreign and self polypeptides (see, Mamula et al. *J. Immunol.* 149:789–795 (1992). Suitable proteins include synthetic polypeptides designed for this purpose or polypeptide sequences from homologous proteins from natural sources, such as proteins encoded by a different allele at the same locus as the self polypeptide.

The compositions also include an adjuvant. As used here, number of adjuvants are well known to one skilled in the art. Suitable adjuvants include incomplete Freund's adjuvant, alum, aluminum phosphate, aluminum hydroxide, N-acetylmuramyl-L-threonyl-D-isoglutamine (thr-MDP), N-acetyl-nor-muramyl-L-alanyl-D-isoglutamine (CGP 11637, referred to as nor-MDP), N-acetylmuramyl-Lalanyl-D-isoglutaminyl-L-alanine-2-(1'-2'-dipalmitoyl-sn-glycero-3-hydroxyphosphoryloxy)-ethylamine (CGP 19835A, referred to as MTP-PE), and RIBI, which contains three components extracted from bacteria, monophosphoryl lipid A, trehalose dimycolate and cell wall skeleton (MPL+TDM+CWS) in a 2% squalene/Tween 80 emulsion. The effectiveness of an adjuvant may be determined by measuring the amount of antibodies directed against the immunogenic peptide.

A particularly useful adjuvant and immunization schedule are described in Kwak et al. *New Eng. J. Med.* 327–1209–1215 (1992). The immunological adjuvant described there comprises 5% (wt/vol) squalene, 2.5% Pluronic L121 polymer and 0.2% polysorbate in phosphate buffered saline.

The concentration of immunogenic peptides of the invention in the pharmaceutical formulations can vary widely, i.e. from less than about 0.1%, usually at or at least about 2% to as much as 20% to 50% or more by weight, and will be selected primarily by fluid volumes, viscosities, etc., in accordance with the particular mode of administration selected.

The peptides of the invention can also be expressed by attenuated viral hosts, such as vaccinia or fowlpox. This approach involves the use of vaccinia virus as a vector to express nucleotide sequences that encode the peptides of the invention. Upon introduction into a host, the recombinant vaccinia virus expresses the immunogenic peptide, and thereby elicits an immune response. Vaccinia vectors and methods useful in immunization protocols are described in, e.g., U.S. Pat. No. 4,722,848. Another vector is BCG (Bacille Calmette Guerin). BCG vectors are described in Stover et al. (*Nature* 351:456–460 (1991)). A wide variety of other vectors useful for therapeutic administration or immunization of the peptides of the invention, e.g., *Salmonella typhi* vectors and the like, will be apparent to those skilled in the art from the description herein.

The DNA encoding one or more of the peptides of the invention can also be administered to the patient. This approach is described, for instance, in Wolff et. al., *Science* 247: 1465–1468 (1990) as well as U.S. Pat. Nos. 5,580,859 and 5,589,466.

In order to enhance serum half-life, the peptides may also be encapsulated, introduced into the lumen of liposomes, prepared as a colloid, or other conventional techniques may be employed which provide an extended serum half-life of the peptides. A variety of methods are available for preparing liposomes, as described in, e.g., Szoka et al., *Ann. Rev. Biophys. Bioeng.* 9:467 (1980), U.S. Pat. Nos. 4, 235,871, 4,501,728 and 4,837,028.

The peptides or antibodies of the invention can also be used for diagnostic purposes. For instance, peptides can be used to screen for autoantibodies to ensure that the vaccination has been effective. Antibodies can be used to detect the presence of particular Chemokine receptor molecules associated with disease.

The following examples are offered by way of illustration, not by way of limitation.

EXAMPLE 1

This example describes a reproducible bioassay for CXCR3 activation.

A stable line transfectant of NSO-1 cells expressing the cDNA for human CXCR3 was prepared according to standard techniques. The surface expression of hu-CXCR3 on the transfectants compared to untransfected parent NSO-1 cells was confirmed by FACS staining using mouse anti-human CXCR3 monoclonal antibody (R&D systems).

To establish a bioassay for CXCR3 activation, the CXCR3 transfectant cells were cultured with either human IP-10, or the mouse anti-human CXCR3 antibody, and the physiological response of the cells was measured using a microphysiometer. This machine measures changes in the pH of the extracellular medium of the cell cultures which result from ligand receptor binding on the cell surface. These extracellular acidification rate measurements have previously been used as markers of antigen specific T cell activation and T cell epitope identification. The current assay is used to provide a biological read out for the identification of chemokine or chemokine receptor peptides involved in binding to IP-10 or agonistic anti-CXCR3 antibody.

The experiments indicated that human IP-10 and anti-CXCR3 antibody both triggered substantial acidification rate changes in the CXCR3 transfectants, as shown in FIG. 1. Importantly, the same ligands induce no change in acidification rate of untransfected NSO-1 cells (FIG. 1).

EXAMPLE 2

This example describes synthesis of human CXCR3 derived peptides.

Figure 2:
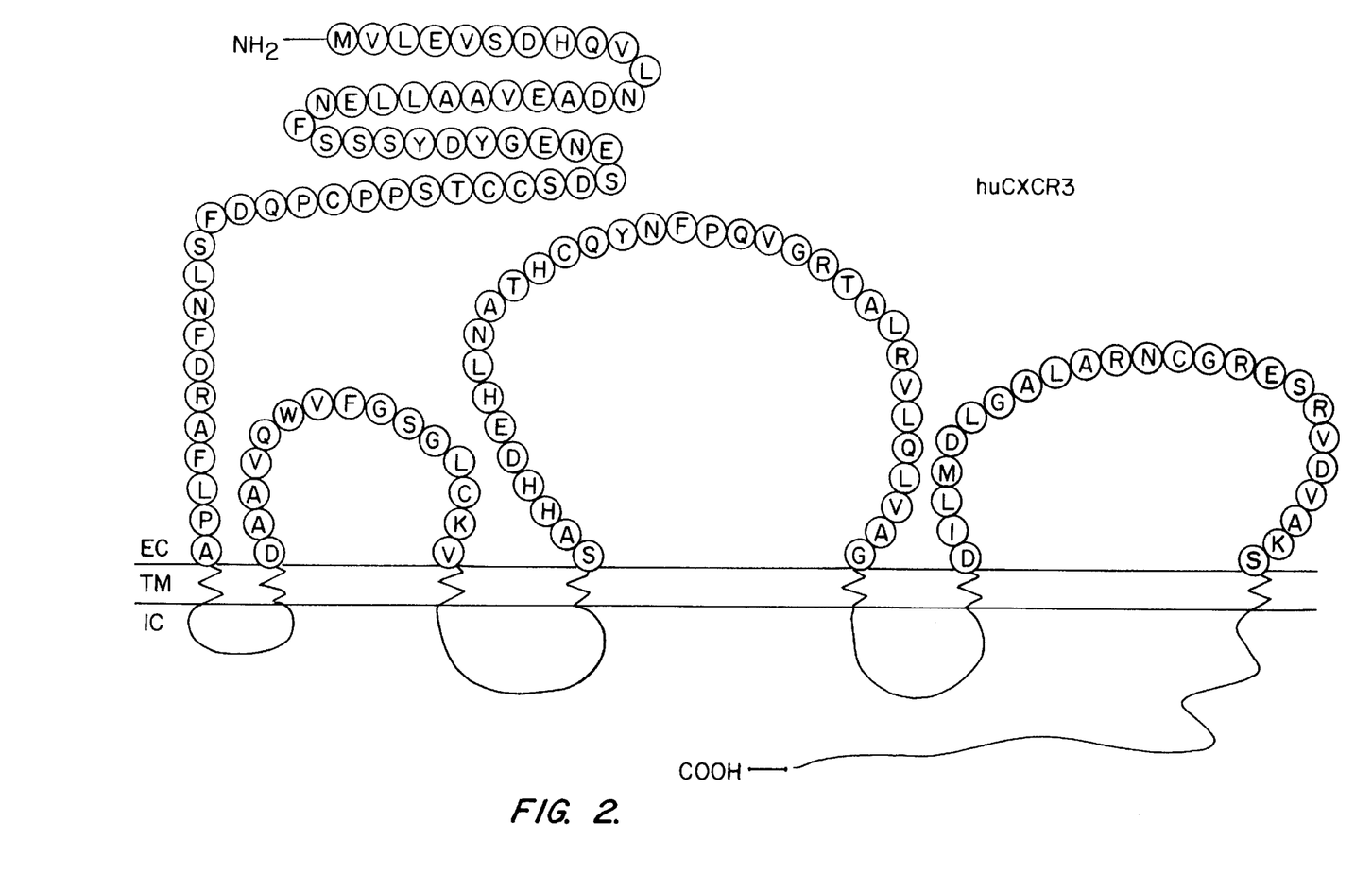
FIG. 2 shows the structure of the seven transmembrane G-protein coupled human CXCR3. Only amino acids in the extracellular domains are given (SEQ ID NOS:8, 4, 9 and 7, respectively).
Figure 3:
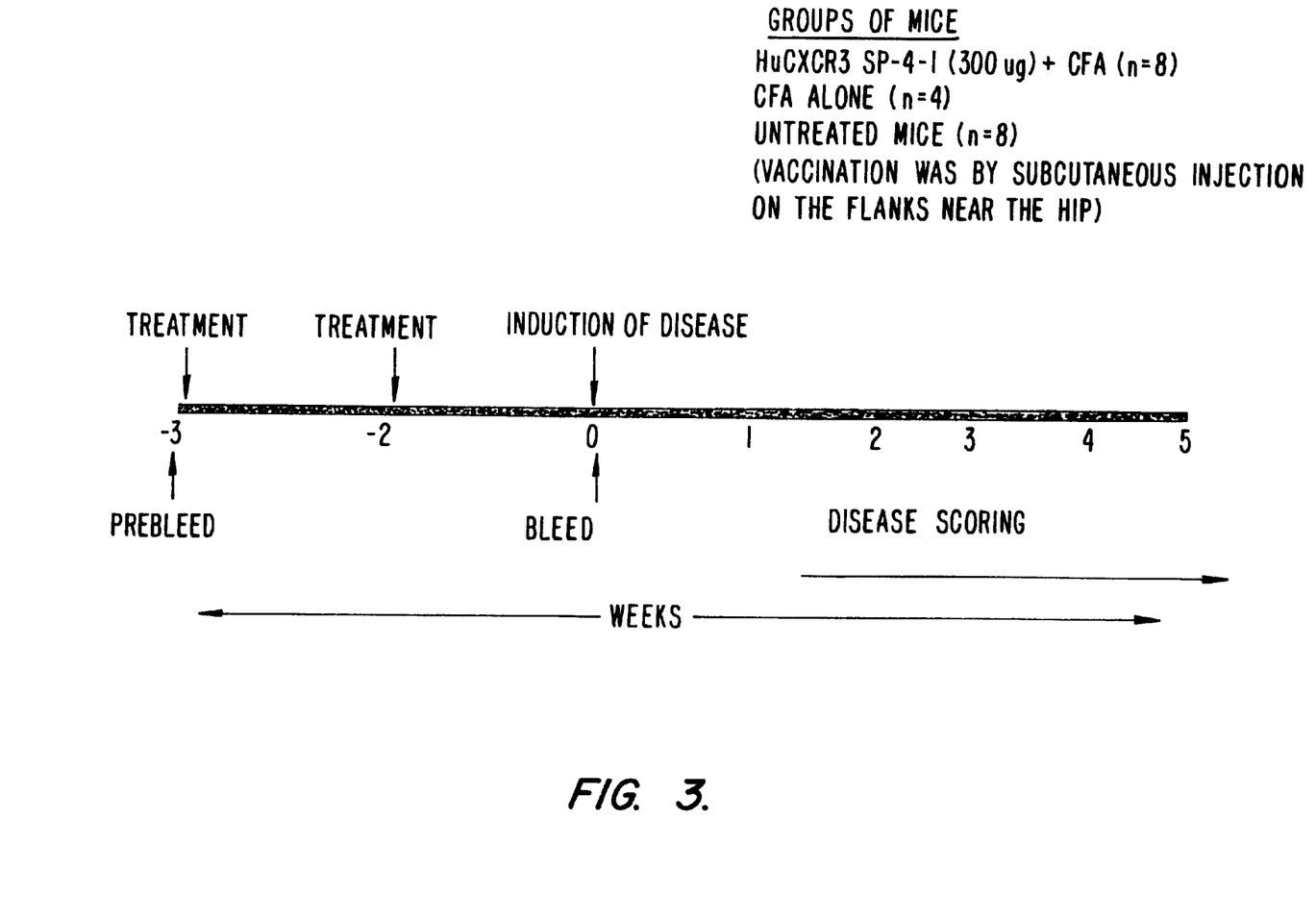
FIG. 3 is a schematic of the experiments in which peptides vaccines of the invention were used to prevent EAE in mice.
Figure 4:
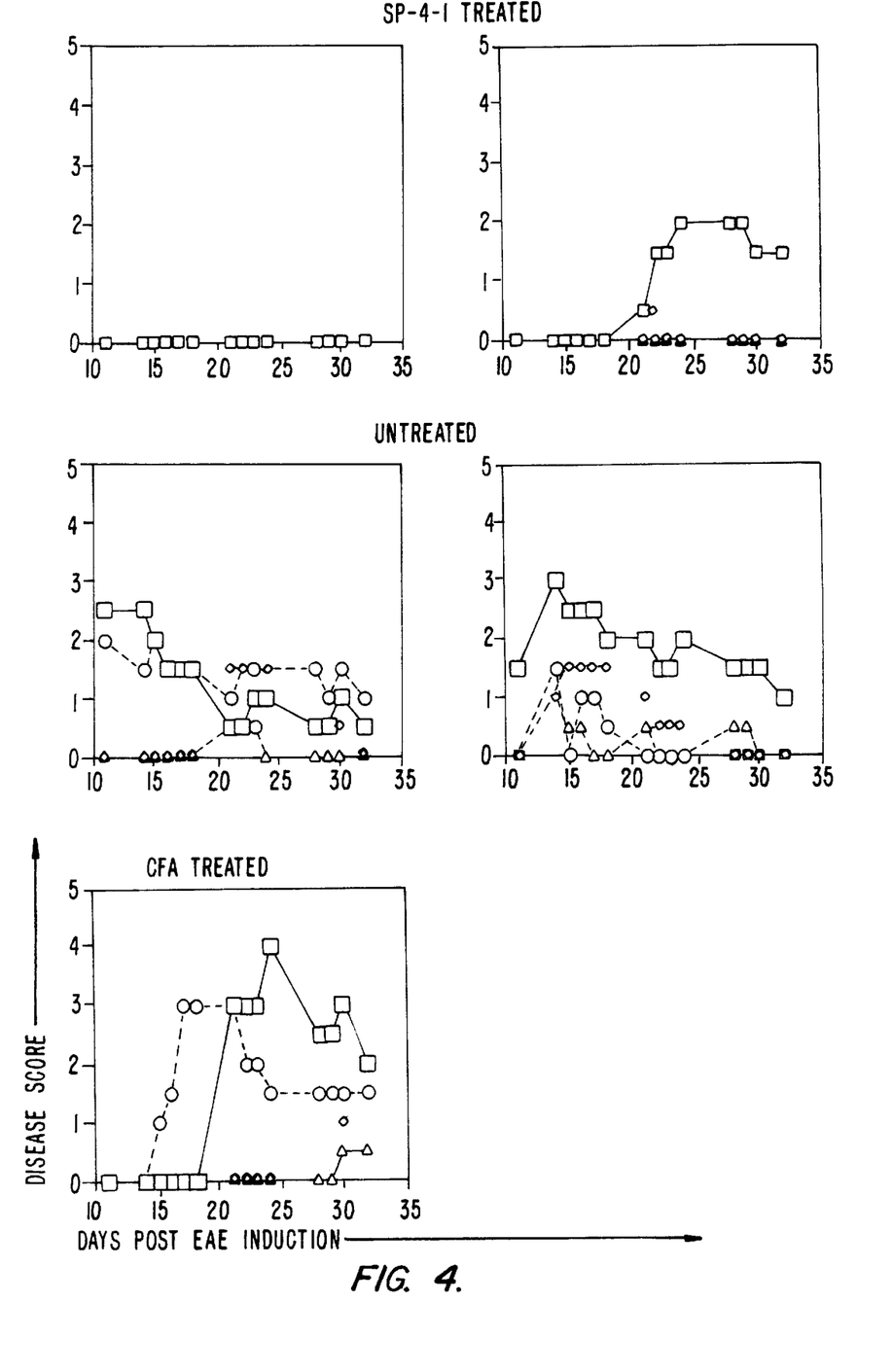
FIG. 4 shows the results of experiments in which peptides vaccines of the invention were used to prevent EAE in mice.

A schematic representation of the surface portion of human CXCR3 is given in FIG. 2. The receptor has 4 surface portions, 4 intracellular portions and seven transmembrane portions. The surface portions were designated starting from N-terminus as SP-1, SP-2, SP-3 and SP-4.

The peptides shown in Table 1 derived from these four surface portions were prepared by solid phase peptide synthesis. The names of the peptides are based on the surface portion of CXCR3 from which they were derived. For example, SP-1-1 means this peptide was derived from the first portion of the CXCR3 protein.

TABLE 1

| Peptide Name | Sequence | SEQ ID NO: |
|---|---|---|
| SP-1-1 | 1 MVLEVSDHQVLNDAEVAALL -NH2 | 10 |
| SP-1-2 | 2 ENFSSSYDYGENESDSCCTS -NH2 | 11 |
| SP-1-3 | 3 PPCPQDFSLNFDRAFLPA -NH2 | 12 |
| SP-2-1 | 4 DAAVQWVFGSGLCKV -NH2 | 13 |
| SP-3-1 | 5 SAHHDERLNATHCQYN -NH2 | 14 |
| SP-3-2 | 6 FPQVGRTALRVLQLVAG -NH2 | 15 |
| SP-4-1 | 7 DILMDLGALARNCGRESRVDVAKS -NH2 | 16 |

The ability of these receptor-derived peptides to bind anti-CXCR3 antibody was evaluated using a standard ELISA format. The peptides were dissolved in 0.1 M bicarbonate buffer and coated on a 96 well ELISA plate overnight. The excess peptides were removed and nonspecific binding sites in the wells were blocked by 0.1% bovine serum albumin. Anti-CXCR3 antibody (0.5 ug/well) was added to these wells and incubated for 2 hours. Excess antibody was removed by washing with PBS. HRP conjugated goat anti-mouse antibody was used as secondary antibody for detection. Two of the seven receptor-derived peptides, namely SP-1-3 and SP-4-1, showed substantial binding to anti-CXCR3 antibody. Further support for the conclusion that anti-CXCR3 antibody bound two of the seven receptor-derived peptides was provided by FACS analysis of the same interactions. These studies revealed that the receptor-derived peptide SP-4-1 potently blocked binding of anti-CXCR3 antibody to the CXCR3 cell line transfectant. The receptor-derived peptide SP-1-3 provided partial inhibition of the binding of the antibody to CXCR3 transfectants. In contrast, an antibody nonbinding receptor-derived peptide, SP-2-1, failed to inhibit binding to CXCR3 transfectants. The data described here collectively demonstrate that anti-CXCR3 antibody can bind to two separate peptide portions of the CXCR3 extracellular domain.

EXAMPLE 3

This example demonstrates that peptide vaccines of the invention can be used to prevent EAE in mice.

Protocols for Animal Experiments:

SJL mice (6–8 weeks old) were obtained from Jackson Laboratories. They were kept in quarantine for two weeks. These mice get EAE when immunized with a peptide from proteolipid protein (PLP). The peptide sequence used for the immunization of these mice is PLP 139-151 and is amidated at the C terminus (HSLGWLGHPDKF-NH2; SEQ ID NO: 17). For the experiments, induction of the disease is considered Day 0. Three weeks before the induction of the disease, the mice were vaccinated with Human CXCR3S-P4-1 peptide mixed with complete Freund's Adjuvant.

Preparation of Peptide CFA Emulsion for Treatment 4 mg of human CXCR3 SP-4-1 peptide was dissolved in 1 ml of phosphate buffered saline pH 7.4 (PBS). One ml of CFA obtained from VWR (Difco, Adjuvant Complete H37RA) was added to the peptide solution and the mixture was sonicated for 5 seconds using a fine tip sonicator. The emulsion was taken in 1 ml syringe (needed 2 syringes) fitted with a 25 gauge needle. Each mouse was given 100 ul of the emulsin under each flank near the hind legs by subcutaneous injection (total volume per mouse=200 ul, total peptide per mouse=200 ug).

Preparation of CFA Alone:

One ml of PBS and 1 ml of CFA were mixed and sonicated for 5 seconds and the emulsin is drawn into a 1 ml syringe fitted with a 25 gauge needle. Each mouse was given 100 ul of this emulsion under each flank near hind legs by subcutaneous injection (total volume of CFA per mouse=200 ul).

Induction of Disease:

To an aqueous solution of peptide (4 mg per ml in PBS) equal volume of CFA was added and the mixture was sonicated for 5 seconds. The emulsion was drawn in a 1 ml syringe fitted with a 25 gauge needle and subcutaneously injected (200 ul total per mouse) in mice at the foot pad and back.

Testing the Antibody Response to SP4-1 Peptide

The mice were bled at week 0 and week 5 and serum was tested by ELISA for the presence of antibodies against the human CXCR3 SP-4-1 peptide. Briefly, the SP4-1 peptide dissolved in 0.1 M sodium bicarbonate buffer was plated on a 96-well ELISA plate overnight. The nonspecific binding sites on the plate were coated with 0.1% bovine serum albumin solution in PBS. The wells were washed and serum (diluted in PBS) was added to the wells and incubated at room temperature for 1.5 hours. The wells were then washed and HRP conjugated anti-mouse immunoglobulin antibody was used to detect the presence of anti-SP4-1 antibodies). The results of this ELISA clearly indicate that the SP4-1 treated mice show an antibody response against this peptide.

Results of FAE Study

Sp4-1 was administered with CFA at 21 days and 14 days before induction of EAE as described above (FIG. 3). The results are shown in FIG. 4. There it can be seen that while most of the untreated and CFA treated mice showed clinical symptoms of EAE, 7 out of 8 mice treated with SP4-1 in CFA showed no clinical symptoms.

The above examples are provided to illustrate the invention but not to limit its scope. Other variants of the invention will be readily apparent to one of ordinary skill in the art and are encompassed by the appended claims. All publications, patents, and patent applications cited herein are hereby incorporated by reference.

What is claimed is:

1. A method of inducing an immune response against a CXCR3 chemokine rereptor molecule in a patient, the method comprising administering to the patient an immunologically effective amount of a pharmaceutical composition comprising an adjuvant and an immunogenic chemokine receptor polypeptide from an extracellular region of a CXCR3 chemokine receptor molecule, wherein the extracellular region is selected from the group consisting of SEQ ID NO:8, SEQ ID NO:4, SSEQ ID NO:9, and SEQ ID NO:7.

2. The method of claim 1, wherein the immunogenic peptide is cyclized.

3. The method of claim 1, wherein the immunogenic chemokine receptor peptide consists of 10 to 50 residues.

4. The method of claim 1, wherein the immunogenic chemokine receptor peptide consists of 15 to 30 residues.

5. The method of claim 1, wherein the immunogenic chemokine receptor polypeptide has an amino acid sequence selected from the group consisting of SEQ ID NO:1, SEQ ID NO:2, SEQ ID NO:3, SEQ ID NO:4, SEQ ID NO:5, SEQ ID NO:6, and SEQ ID NO:7.

6. The method of claim 1, wherein the administration is parenteral.

7. The method of claim 1, wherein the adjuvant is alum.

8. A method of inhibiting recruitment of T cells to an inflammation site in a patient, the method comprising administering to the patient an immunologically effective amount of a pharmaceutical composition comprising an adjuvant and an immunogenic chemokine receptor peptide from an extracellular region of a CXCR3 chemokine receptor molecule, wherein the extracellular region is selected from the group consisting of SEQ ID NO:8, SEQ ID NO:4, SEQ ID NO:9, and SEQ ID NO:7.

9. The method of claim 8, wherein the immunogenic peptide is cyclized.

10. The method of claim 8, wherein the immunogenic chemokine receptor peptide consists of 10 to 50 residues.

11. The method of claim 8, wherein the immunogenic chemokine receptor peptide consists of 15 to 30 residues.

12. The method of claim 8, wherein the immunogenic chemokine receptor polypeptide has an amino acid sequence selected from the group consisting of SEQ ID NO:1, SEQ ID NO:2, SEQ ID NO:3, SEQ ID NO:4, SEQ ID NO:5, SEQ ID NO:6, and SEQ ID NO:7.

13. The method of claim 8, wherein the inflammatory response is associated with multiple sclerosis.

14. A pharmaceutical composition comprising an adjuvant and an isolated immunogenic chemokine receptor polypeptide from an extracellular region of a CXCR3 chemokine receptor molecule, wherein the extracellular region is selected from the group consisting of SEQ ID NO:8, SEQ ID NO:4, SEQ ID NO:9, and SEQ ID NO:7.

15. The composition of claim 14, wherein the immunogenic peptide is cyclized.

16. The composition of claim 14, wherein the immunogenic chemokine receptor peptide consists of 10 to 50 residues.

17. The composition of claim 14, wherein the immunogenic chemokine receptor peptide consists of 15 to 30 residues.

18. The composition of claim 14, wherein the immunogenic chemokine receptor polypeptide has an amino acid sequence selected from the group consisting of SEQ ID NO:1, SEQ ID NO:2, SEQ ID NO:3, SEQ ID NO:4, SEQ ID NO:5, SEQ ID NO:6, and SEQ ID NO:7.

19. A method of inducing an immune response against a chemokine receptor molecule in a patient, the method comprising administering to the patient an immunologically effective amount of a pharmaceutical composition comprising an adjuvant and an immunogenic chemokine receptor polypeptide from a extracellular region of said chemokine receptor molecule, wherein said immunogenic chemokine receptor polypeptide has an amino acid sequence selected from the group consisting of SEQ ID NO:1, SEQ ID NO:2, SEQ ID NO:3, SEQ ID NO:4, SEQ ID NO:5, SEQ ID NO:6, and SEQ ID NO:7.

20. The method of claim 19, wherein said immunogenic chemokine receptor polypeptide is SEQ ID NO: 1.

21. The method of claim 19, wherein said immunogenic chemokine receptor polypeptide is SEQ ID NO:2.

22. The method of claim 19, wherein said immunogenic chemokine receptor polypeptide is SEQ ID NO:3.

23. The method of claim 19, wherein said immunogenic chemokine receptor polypeptide is SEQ ID NO:4.

24. The method of claim 19, wherein said immunogenic chemokine receptor polypeptide is SEQ ID NO:5.

25. The method of claim 19, wherein said immunogenic chemokine receptor polypeptide is SEQ ID NO:6.

26. The method of claim 19, wherein said immunogenic chemokine receptor polypeptide is SEQ ID NO:7.

27. A method of inhibiting recruitment of T cells to inflammation site in a patient, the method comprising administering to the patient an immunologically effective amount of a pharmaceutical composition comprising an adjuvant and an immunogenic chemokine receptor peptide from an extracellular region of a chemokine receptor molecule, wherein said immunogenic chemokine receptor polypeptide has an amino acid sequence selected from the group consisting of SEQ ID NO:1, SEQ ID NO:2, SEQ ID NO:3, SEQ ID NO:4, SEQ ID NO:5, SEQ ID NO:6, and SEQ ID NO:7.

28. The method of claim 27, wherein said immunogenic chemokine receptor polypeptide is SEQ ID NO: 1.

29. The method of claim 27, wherein said immunogenic chemokine receptor polypeptide is SEQ ID NO: 2.

30. The method of claim 27, wherein said immunogenic chemokine receptor polypeptide is SEQ ID NO: 3.

31. The method of claim 27, wherein said immunogenic chemokine receptor polypeptide is SEQ ID NO: 4.

32. The method of claim 27, wherein said immunogenic chemokine receptor polypeptide is SEQ ID NO: 5.

33. The method of claim 27, wherein said immunogenic chemokine receptor polypeptide is SEQ ID NO: 6.

34. The method of claim 27, wherein said immunogenic chemokine receptor polypeptide is SEQ ID NO: 7.

35. A pharmaceutical composition comprising an adjuvant and an isolated immunogenic chemokine receptor polypeptide from an extracellular region of a chemokine receptor molecule, wherein said immunogenic chemokine receptor polypeptide has an amino acid sequence selected from the group consisting of SEQ ID NO:1, SEQ ID NO:2, SEQ ID NO:3, SEQ ID NO:4, SEQ ID NO:5, SEQ ID NO:6, and SEQ ID NO:7.

36. The pharmaceutical composition of claim 34, wherein said immunogenic chemokine receptor polypeptide is SEQ ID NO:1.

37. The pharmaceutical composition of claim 34, wherein said immunogenic chemokine receptor polypeptide is SEQ ID NO:2.

38. The pharmaceutical composition of claim 34, wherein said immunogenic chemokine receptor polypeptide is SEQ ID NO:3.

39. The pharmaceutical composition of claim 34, wherein said immunogenic chemokine receptor polypeptide is SEQ ID NO:4.

40. The pharmaceutical composition of claim 34, wherein said immunogenic chemokine receptor polypeptide is SEQ ID NO:5.

41. The pharmaceutical composition of claim 34, wherein said immunogenic chemokine receptor polypeptide is SEQ ID NO:6.

42. The pharmaceutical composition of claim 34, wherein said immunogenic chemokine receptor polypeptide is SEQ ID NO:7.

* * * * *